United States Patent
Sinkel et al.

(10) Patent No.: US 9,540,661 B2
(45) Date of Patent: Jan. 10, 2017

(54) METHOD FOR THE COMPLETE ANAEROBIC DIGESTION OF POLYMER MIXTURES

(71) Applicant: BASF SE, Ludwigshafen (DE)

(72) Inventors: Carsten Sinkel, Mannheim (DE); Robert Loos, Ludwigshafen, DE (US); Karlheinz Jochem, Lingenfeld (DE); Kai Oliver Siegenthaler, Mannheim (DE); Xin Yang, Bensheim (DE); Ulf Küper, Mannheim (DE); Mathias Zimmermann, Worms (DE)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 13/937,683

(22) Filed: Jul. 9, 2013

(65) Prior Publication Data
US 2014/0080196 A1    Mar. 20, 2014

Related U.S. Application Data

(60) Provisional application No. 61/669,178, filed on Jul. 9, 2012.

(51) Int. Cl.
*C12P 5/02*    (2006.01)

(52) U.S. Cl.
CPC .............. *C12P 5/023* (2013.01); *Y02E 50/343* (2013.01)

(58) Field of Classification Search
IPC ..................................................... C12P 5/023
See application file for complete search history.

(56) References Cited

U.S. PATENT DOCUMENTS

| | | | |
|---|---|---|---|
| 5,281,691 A | 1/1994 | Hubbs et al. | |
| 5,286,770 A | 2/1994 | Bastioli et al. | |
| 5,847,207 A | 12/1998 | Suchsland et al. | |
| 5,874,486 A | 2/1999 | Bastioli et al. | |
| 5,883,199 A | 3/1999 | McCarthy et al. | |
| 6,018,004 A | 1/2000 | Warzelhan et al. | |
| 2004/0225269 A1 | 11/2004 | Zhao et al. | |
| 2005/0154114 A1* | 7/2005 | Hale | 524/436 |
| 2011/0034662 A1 | 2/2011 | Witt et al. | |
| 2011/0039999 A1 | 2/2011 | Witt et al. | |
| 2011/0313075 A1 | 12/2011 | Siegenthaler et al. | |

FOREIGN PATENT DOCUMENTS

| | | |
|---|---|---|
| EP | 488617 A2 | 6/1992 |
| WO | WO-92/09654 A2 | 6/1992 |
| WO | WO-96/5173 A1 | 2/1996 |
| WO | WO-99/64498 A1 | 12/1999 |
| WO | WO-2008/010296 A1 | 1/2008 |
| WO | WO-2009/024294 A1 | 2/2009 |
| WO | WO-2009/127555 A1 | 10/2009 |
| WO | WO-2009/127556 A1 | 10/2009 |
| WO | WO-2010/034711 A1 | 4/2010 |
| WO | WO-2010/151798 A2 | 12/2010 |

\* cited by examiner

*Primary Examiner* — Rosanne Kosson
(74) *Attorney, Agent, or Firm* — Drinker Biddle & Reath LLP

(57) ABSTRACT

The present invention relates to a process for complete anaerobic digestion of polymer mixtures of the composition:
  a) 25 to 95% by weight of a polyhydroxyalkanoate selected from the group consisting of poly-4-hydroxybutyrate, poly-3-hydroxybutyrate, poly(3-hydroxybutyrate-co-3-hydroxyvalerate), poly(3-hydroxybutyrate-co-3-hydroxyhexanoate) and poly(3-hydroxybutyrate-co-4-hydroxybutyrate) and
  b) 5 to 75% by weight of an aliphatic polyester comprising:
    i) 65 to 100 mol %, based on components i to ii, of succinic acid or of a succinic acid derivative;
    ii) 0 to 35 mol %, based on components i to ii, of an aliphatic $C_5$-$C_{36}$-dicarboxylic acid, of a corresponding acid derivative or of a mixture;
    iii) 98 to 100 mol %, based on components i to ii, of a $C_2$-$C_8$-alkylenediol or $C_2$-$C_6$-oxyalkylenediol;
    iv) 0 to 2% by weight, based on the polymer obtainable from components i to iii, of at least one polyfunctional compound comprising at least two isocyanate, isocyanurate, oxazoline or epoxide groups or at least three alcohol or carboxylic acid groups.

12 Claims, No Drawings

METHOD FOR THE COMPLETE ANAEROBIC DIGESTION OF POLYMER MIXTURES

CROSS-REFERENCE TO RELATED APPLICATIONS

This application claims benefit (under 35 USC 119(e)) of U.S. Provisional Application 61/669,178, filed Jul. 9, 2012, which is incorporated by reference.

FIELD OF THE INVENTION

The present invention relates to a process for complete anaerobic digestion of polymer mixtures of the composition:
a) 25 to 95% by weight of a polyhydroxyalkanoate selected from the group consisting of poly-4-hydroxybutyrate, poly-3-hydroxybutyrate, poly(3-hydroxybutyrate-co-3-hydroxyvalerate), poly(3-hydroxybutyrate-co-3-hydroxyhexanoate) and poly(3-hydroxybutyrate-co-4-hydroxybutyrate) and
b) 5 to 75% by weight of an aliphatic polyester comprising:
  i) 65 to 100 mol %, based on components i to ii, of succinic acid or of a succinic acid derivative;
  0 to 35 mol %, based on components i to ii, of an aliphatic $C_5$-$C_{36}$-dicarboxylic acid, of a corresponding acid derivative or of a mixture;
  iii) 98 to 100 mol %, based on components i to ii, of a $C_2$-$C_8$-alkylenediol or $C_2$-$C_6$-oxyalkylenediol;
  iv) 0 to 2% by weight, based on the polymer obtainable from components i to iii, of at least one polyfunctional compound comprising at least two isocyanate, isocyanurate, oxazoline or epoxide groups or at least three alcohol or carboxylic acid groups.

BACKGROUND OF THE INVENTION

WO 2010/151798 describes the addition of aliphatic polyesters such as polybutylene succinate (PBS) and polybutylene succinate-co-adipate (PBSA) in order to reduce the aerobic biodegradability of polyhydroxyalkanoate articles. The anaerobic digestion of the abovementioned polymer mixtures is not mentioned in WO 2010/151798.

Under anaerobic conditions, aliphatic polyesters such as PBS, polybutylene succinate-co-sebacate (PBSSe) and PBSA are not degraded. Polyhydroxyalkanoates (PHA), in contrast, are degraded under anaerobic conditions. In analogy to the results found in WO 2010/151798, it is to be expected that, in a compound consisting of components a) and b), no more than component a) (PHA) will be degraded, while component b) remains. With b) in the continuous phase, it can even be expected that the degradation of the disperse PHA phase will be significantly disrupted or even inhibited.

US 2004/025552269 describes the anaerobic digestion of polymer mixtures comprising 15% by weight of polybutylene succinate-co-adipate and a mixture of various polyhydroxyalkanoates. The digestion rates after 28 days are 30% lower than the digestion rate of mixtures comprising exclusively polyhydroxyalkanoates. Under the conditions specified in US 2004/025552269, the polybutylene succinate-co-adipate is apparently not digested; there is accordingly no complete anaerobic digestion of the polymer mixture.

In the biological treatment of organic wastes, the process of anaerobic fermentation is becoming more important.

In contrast to biodegradation under aerobic conditions, in which $CO_2$ forms as the terminal metabolic product, biodegradation under anaerobic conditions leads not only to $CO_2$ but additionally to $CH_4$ as a metabolic end product, which is utilizable for energy purposes. The mixture of carbon dioxide, methane and traces of further gases which is formed in the course of anaerobic fermentation is called biogas.

By virtue of the energy recovery, the process of anaerobic fermentation, optionally coupled with subsequent aerobic composting, has advantages over purely aerobic composting (cold combustion).

The polyhydroxyalkanoates generally have low melt strength and—closely connected to this—low strain viscosity/strain hardening. They can therefore be processed further to films only with difficulty in standard production processes, for example film blowing.

SUMMARY OF THE INVENTION

The aim of the present invention was accordingly to find polymer mixtures which can be processed to films or coatings, and at the same time are degradable under anaerobic conditions to give biogas.

In polymer mixtures of polymer components a) and b), no more than the degradation of the polyhydroxyalkanoate a) is expected, and not that of component b). This is also the case in mixtures of starch or else PLA and b) (within the industrially relevant periods under consideration). Interestingly, polymer mixtures comprising polymer component b in the ratios claimed, in mixtures with polyhydroxyalkanoates (polymer component a), have significantly enhanced anaerobic digestibility far exceeding the calculated value for the polyhydroxyalkanoate content. This is surprising and suggests that the inventive polymer mixtures have synergism with regard to anaerobic digestion. This synergism was not found in mixtures of b) with another natural polymer such as thermoplasticized starch.

Especially in the case of films or coatings comprising polymer component b) in 50 to 75% by weight, which thus constitutes the continuous phase in the mixture, significant biogas formation under anaerobic conditions was not to be expected.

Use of the mixtures of components a and b described at the outset surprisingly makes it possible to produce mechanically durable films with high anaerobic digestibility.

The invention is described in detail hereinafter.

DETAILED DESCRIPTION OF THE INVENTION

Polyhydroxyalkanoates (polymer component a) are primarily understood to mean poly-4-hydroxybutyrates and poly-3-hydroxybutyrates or poly-3-hydroxybutyrate-co-4-hydroxybutyrates, and also copolyesters of the aforementioned poly-3-hydroxybutyrates with 3-hydroxyvalerate, 3-hydroxyhexanoate and/or 3-hydroxyoctanoate. Poly-3-hydroxybutyrates are sold, for example, by PHB Industrial under the Biocycle® brand name and by Tianan under the Enmat® name.

Poly-3-hydroxybutyrate-co-4-hydroxybutyrates are known, particularly from Metabolix. They are sold under the Mirel® trade name.

Poly-3-hydroxybutyrate-co-3-hydroxyhexanoates are known, for example, from Kaneka. Poly-3-hydroxybutyrate-co-3-hydroxyhexanoates generally have a 3-hydroxyhexanoate content of 1 to 20 and preferably of 3 to 15 mol % based on the butyrate content.

Synergism in the course of anaerobic digestion is found for all aforementioned polyhydroxyalkanoates. It is particularly marked in the case of the copolymers: poly-3-hydroxybutyrate-co-3-hydroxyvalerate and especially in the case of poly-3-hydroxybutyrate-co-4-hydroxybutyrate and poly-3-hydroxybutyrate-co-3-hydroxyhexanoate. The aforementioned copolymers are particularly preferred for the inventive polymer mixtures.

The polyhydroxyalkanoates generally have a molecular weight Mw of 100 000 to 1 000 000 and preferably of 300 000 to 600 000.

The aliphatic polyesters (polymer component b) suitable for the invention are described in detail, for example, in WO 2010/034711.

The aliphatic polyesters b generally have the following makeup:

i) 65 to 100 mol %, preferably 75 to 98 mol %, based on components i to ii, of succinic acid or of a succinic acid derivative;
ii) 35 to 0 mol %, preferably 25 to 2 mol %, based on components i to ii, of an aliphatic $C_5$-$C_{36}$-dicarboxylic acid: especially adipic acid, suberic acid, azelaic acid, sebacic acid and/or brassylic acid or a corresponding acid derivative or a mixture;
iii) 98 to 100 mol %, based on components i to ii, of a $C_2$-$C_6$-alkylenediol or $C_2$-$C_6$-oxyalkylenediol and
iv) 0 to 2% by weight, based on the total weight of components i to iii, of a chain extender or branching agent, preferably 0.05 to 2% by weight, based on the total weight of components i to iii, of a chain extender or branching agent and especially of a diisocyanate.

The polyesters described are preferably synthesized in a direct polycondensation reaction of the individual components. The dicarboxylic acid derivatives are converted together with the diol in the presence of a transesterification catalyst directly to the polycondensate of high molecular weight. On the other hand, the preferred copolyester can also be obtained by transesterification of polybutylene succinate (PBS), adipic acid, suberic acid, azelaic acid, sebacic acid, brassylic acid and/or octadecanedioic acid in the presence of diol. The catalysts used are typically zinc catalysts, aluminum catalysts and especially titanium catalysts. Titanium catalysts such as tetraisopropyl orthotitanate and especially tetraisobutoxy orthotitanate (TBOT) have the advantage over the tin, antimony, cobalt and lead catalysts frequently used in the literature, for example tin dioctanoate, that residual amounts of the catalyst or conversion product of the catalyst remaining in the product are less toxic. This fact is particularly important in the case of the biodegradable polyesters, since they get directly into the environment, for example, in the form of composting bags or mulch films.

The succinic acid or a mixture of the dicarboxylic acids or the respective carboxylic acid derivatives are generally heated in the presence of an excess of diol together with the catalyst and optionally a branching agent, generally at first to an internal temperature of 170 to 230° C. over a period of approximately 60-180 min, and water formed and excess diol are distilled off. Subsequently, the melt of the prepolyester thus obtained is typically condensed up to the desired viscosity with a viscosity number (VN) of 100 to 450 ml/g and preferably 120 to 250 ml/g at an internal temperature of 200 to 250° C. at reduced pressure with distillative removal of diol released over several hours. The desired viscosity can preferably additionally be established with the aid of a chain extender, for example of a diisocyanate.

The chain-extended aliphatic polyesters b can be prepared, for example, by the methods described in WO 96/15173 and EP-A 488 617. It has been found to be advantageous first to convert components i to iii to a prepolyester having a VN of 50 to 100 ml/g, preferably 60 to 80 ml/g, and then to react them with chain extenders iv, for example with diisocyanates or with epoxide-containing polymethacrylates in a chain extension reaction to give a polyester having a VN of 100 to 450 ml/g, preferably 120 to 250 ml/g.

Polyesters such as PBS are commercially available, for example, under the Bionolle® brand name from Showa Highpolymer.

Synergism in the course of anaerobic digestion is found for all aforementioned aliphatic polyesters as component b. It is particularly marked for the aliphatic copolymers such as the polyesters or polybutylene succinate-co-adipate (PBSA) described in WO 2010/034711, for example.

The acid component i used here is 75 to 98 mol %, preferably 80 to 95 mol %, based on components i to ii, of succinic acid. Succinic acid is obtainable by a petrochemical route and preferably from renewable raw materials as described, for example, in WO 2009/024294. WO 2009/024294 discloses a biotechnological method for production of succinic acid and 1,4-butanediol, proceeding from different carbohydrates with microorganisms from the class of the Pasteurellaceae.

Acid component ii is used in 25 to 2 mol %, preferably 20 to 5 mol %, based on components i to ii.

The dicarboxylic acids ii are understood to mean aliphatic $C_5$-$C_{36}$-dicarboxylic acids such as, more particularly, adipic acid, suberic acid, azelaic acid, sebacic acid and/or brassylic acid. Azelaic acid, sebacic acid and/or brassylic acid are particularly preferred. The abovementioned acids are obtainable from renewable raw materials. For example, sebacic acid is obtainable from castor oil. Such polyesters feature excellent biodegradation characteristics [literature: Polym. Degr. Stab. 2004, 85, 855-863].

The dicarboxylic acids i and ii can be used either as the free acid or in the form of ester-forming derivatives. Ester-forming derivatives are especially the to di-$C_1$-$C_6$-alkyl esters, such as dimethyl, diethyl, di-n-propyl, diisopropyl, di-n-butyl, diisobutyl, di-t-butyl, di-n-pentyl, diisopentyl or di-n-hexyl esters. Anhydrides of the dicarboxylic acids can likewise be used.

The dicarboxylic acids or their ester-forming derivatives can be used individually or as a mixture.

The diols are generally $C_2$-$C_8$-alkylenediols or $C_2$-$C_6$-oxyalkylenediols, and especially 1,3-propanediol and 1,4-butanediol. The latter are likewise obtainable from renewable raw materials. It is also possible to use mixtures of the two diols. Due to the higher melting temperatures and better crystallization of the copolymer formed, 1,4-butanediol is preferred as the diol.

In general, on commencement of the polymerization, the diol (component iii) is used relative to the acids (components i and ii) in a ratio of diol to diacids of 1.0 to 2.5:1 and preferably 1.3 to 2.2:1. Excess amounts of diol are drawn off during the polymerization, such that an approximately equimolar ratio is established at the end of the polymerization. "Approximately equimolar" is understood to mean a diol/diacids ratio of 0.90 to 1.10.

In general, 0 to 1% by weight, preferably 0.01 to 0.9% by weight and especially preferably 0.05 to 0.3% by weight, based on the total weight of components i to iii, of a branching agent iv and/or 0 to 2% by weight, preferably 0.05 to 2% by weight and especially preferably 0.3 to 1% by weight, based on the total weight of components i to iii, of a chain extender iv' selected from the group consisting of: a polyfunctional isocyanate, isocyanurate, oxazoline, carboxylic anhydride such as maleic anhydride, epoxide (especially an epoxide-containing poly(meth)acrylate), an at least trifunctional alcohol or an at least trifunctional carboxylic acid are used. Useful chain extenders iv' include polyfunctional and especially difunctional isocyanates, isocyanurates, oxazolines or epoxides.

Chain extenders and alcohols or carboxylic acid derivatives having at least three functional groups can also be regarded as branching agents. Particularly preferred compounds have three to six functional groups. Examples include: tartaric acid, citric acid, malic acid, trimesic acid, trimellitic acid, trimellitic anhydride, pyromellitic acid and pyromellitic dianhydride; trimethylolpropane, trimethylolethane; pentaerythritol, polyethertriols and glycerol. Preference is given to polyols such as trimethylolpropane, pentaerythritol and especially glycerol.

By means of components iv and/or iv', which can also be referred to as long-chain-branching agents, it is possible to prepare polyesters with improved rheological characteristics. Compounds Iv and iv' ensure good strain hardening/strain viscosity and thus increase process stability in the course of film production.

In general, it is advisable to add the branching (at least trifunctional) compounds at a comparatively early point in the polymerization.

Suitable bifunctional chain extenders are understood to mean, for example, tolylene 2,4-diisocyanate, tolylene 2,6-diisocyanate, diphenylmethane 2,2'-diisocyanate, diphenylmethane 2,4'-diisocyanate, diphenylmethane 4,4'-diisocyanate, naphthylene 1,5-diisocyanate or xylylene diisocyanate, hexamethylene 1,6-diisocyanate, isophorone diisocyanate or methylenebis(4-isocyanatocyclohexane). Particularly preferred are isophorone diisocyanate and especially hexamethylene 1,6-diisocyanate.

The polyesters b generally have a number-average molecular weight (Mn) in the range from 5000 to 100 000, especially in the range from 10 000 to 75 000 g/mol, preferably in the range from 15 000 to 50 000 g/mol, a weight-average molecular weight (Mw) from 30 000 to 300 000, preferably 60 000 to 200 000 g/mol, and an Mw/Mn ratio of 1 to 10, preferably 2 to 8. The viscosity number is between 30 and 450, preferably from 50 to 400 ml/g (measured in o-dichlorobenzene/phenol (weight ratio 50/50)). The melting point is in the range from 85 to 130, preferably in the range from 90 to 120° C.

Aliphatic polyesters b are understood to mean especially polyesters such as polybutylene succinate (PBS), polybutylene succinate-co-adipate (PBSA), polybutylene succinate-co-sebacate (PBSSe), polybutylene succinate-co-azelate (PBSAz) or polybutylene succinate-co-brassylate (PBSBr). The aliphatic polyesters PBS and PBSA are marketed, for example, by Showa Highpolymer under the Bionolle® name and by Mitsubishi under the GSPla® name. More recent developments are described in WO 2010/034711.

The polymer mixtures a, b comprise generally 25 to 95% by weight of polyhydroxyalkanoate (a) and correspondingly 5 to 75% by weight of polyester component b.

Also especially preferred are polymer mixtures a, b in which the polymer component b constitutes the continuous phase. Films formed from such polymer mixtures have excellent mechanical properties. In addition, the polymer mixtures have been virtually completely degraded under anaerobic conditions after 3 weeks, which is extremely surprising due to their comparatively low polyhydroxyalkanoate content. For the reasons mentioned above, polymer mixtures a, b comprising 25 to 55% by weight, preferably 25 to 50% by weight, of polyhydroxyalkanoate (a) and correspondingly 45 to 75% by weight, preferably 50 to 75% by weight, of polyester component b are especially preferred.

Polymer mixtures a, b generally comprise further additives c. In a preferred embodiment, 1 to 50% by weight, based on the total weight of polymer components a to c, of an organic filler is added, selected from the group consisting of: native or plasticized starch, natural fibers, wood flour, comminuted cork, ground bark, nutshells, ground presscake (vegetable oil refinery), dried production residues from the fermentation or distillation of drinks, for example beer, brewed lemonades (e.g. Bionade), wine or sake, and/or of an inorganic filler selected from the group consisting of: chalk, graphite, gypsum, conductive black, iron oxide, calcium chloride, dolomite, kaolin, silica (quartz), sodium carbonate, titanium dioxide, silicate, wollastonite, mica, montmorillonite, talc, glass fibers and mineral fibers.

Starch and amylose may be native, i.e. non-thermoplasticized, or may have been thermoplasticized with plasticizers, for example glycerol or sorbitol (EP-A 539 541, EP-A 575 349, EP 652 910). Thermoplasticized starch is especially preferred because it is itself likewise anaerobically digested, and films comprising polymer components a and b in addition to starch give good mechanical values. Mixtures of starch and polymer component b (without polymer component a) do not exhibit any synergism in terms of anaerobic digestibility. Only the starch is degraded. If starch is added to the polymer mixture of a and b, in addition to the digestion of the starch, the above-described synergistic anaerobic digestion characteristics are also found. The thermoplasticized starch is added to the polymer mixtures comprising components a and b generally in a ratio of 0 to 50, preferably 5 to 35 and especially preferably 10 to 35% by weight. Films produced therefrom have outstanding tear propagation resistance and, at the same time, very good anaerobic digestibility. They are especially suitable for production of thin films.

Natural fibers are, for example, understood to mean cellulose fibers, hemp fibers, sisal, kenaf, jute, flax, abacca, coconut fibers, or else regenerated cellulose fibers (rayon) such as Cordenka fibers.

Addition of mineral fillers, such as chalk, graphite, gypsum, conductive black, iron oxide, calcium chloride, dolomite, kaolin, silica (quartz), sodium carbonate, titanium dioxide, silicate, wollastonite, mica, montmorillonite or talc, can significantly improve the mechanical properties of the films, for example tear propagation resistance. In general, the mineral fillers are used in a concentration of 1 to 50%, preferably 4 to 30% and especially preferably 8 to 25% by weight, based on the polymer components i to iv.

Polyester mixtures a, b may comprise further polymers such as polylactic acid, polycaprolactone, polyglycolic acid, polypropylene carbonate or especially aliphatic-aromatic polyesters, for example polybutylene adipate-coterephthalate, in an amount of 1 to 50% by weight, preferably 20 to 40% by weight, based on the polymer mixtures a and b, in order to alter the profile of properties of the films or coatings.

The biodegradable polyester mixtures may comprise further ingredients which are known to those skilled in the art but are not essential to the invention. For example, the additives customary in the plastics industry, such as stabilizers; nucleating agents; neutralizing agents; lubricants and release agents such as stearates (especially calcium stearate) or erucamide or behenamide; plasticizers, for example citric esters (especially acetyl tributyl citrate), glyceryl esters such as triacetylglycerol or ethylene glycol derivatives, surfactants such as polysorbates, palmitates or laurates; waxes, for example beeswax or beeswax esters; antistats, UV absorbers; UV stabilizers; antifogging agents or dyes. The additives are used in concentrations of 0 to 5% by weight, especially 0.1 to 2% by weight, based on the inventive polyesters. Plasticizers may be present in the inventive polyesters in 0.1 to 10% by weight.

The inventive biodegradable polyester mixtures can be produced from the individual components by known methods (EP 792 309 and U.S. Pat. No. 5,883,199). For example, all mixing partners can be mixed and reacted in one process step in the mixing apparatus known to those skilled in the art, for example kneaders or extruders, at elevated temperatures, for example from 120° C. to 250° C.

The polymer mixtures themselves may comprise 0.05 to 2% by weight of a compatibilizer. Preferred compatibilizers are carboxylic anhydrides such as maleic anhydride and especially the above-described copolymers containing epoxide groups and based on styrene, acrylic esters and/or methacrylic esters. The units bearing epoxide groups are preferably glycidyl(meth)acrylates. Copolymers containing epoxide groups of the abovementioned type are sold, for example, by BASF Resins B. V. under the Joncryl® ADR brand. One example of a particularly suitable compatibilizer is Joncryl® ADR 4368.

Component iv, the aforementioned fillers or the other aforementioned assistants are preferably added to polymer component a or b through previously produced masterbatches of the assistants.

The process of degradation of polymers is explained in detail hereinafter, and the differences between abiotic, aerobic and anaerobic digestion are discussed in detail.

In general, polymers or polymer mixtures may be subject to a degradation process in two fundamentally different ways. First, the polymeric structure of a macromolecule can be broken up exclusively under the influence of abiotic factors (physicochemical parameters, for example: UV radiation, temperature, pH, humidity, influence of reactive oxygen species), which ultimately leads to conversion of the polymer to oligomers, monomers or reaction products resulting from the degradation. This contrasts with the biodegradation of polymers, which is based primarily on the biochemical interaction of microorganisms (bacteria, archaea, fungi) with the polymer. The breaking of the chemical bonds in the polymer is achieved here by specific interactions with the enzymes of the microorganisms. The interplay of a wide variety of different microorganisms and enzymes thereof finally leads to mineralization of the polymer. Mineralization does not just convert the polymer back to monomers or oligomers, but converts it enzymatically to the microbial metabolic end products water, carbon dioxide and methane (under anaerobic conditions). Abiotic degradation and biodegradation frequently also proceed in parallel—what is crucial, however, is that mineralization is at the end of the biodegradation.

Both the biodegradation and the physicochemical degradation of polymers lead to a loss of the characteristic polymer properties.

The biodegradation of macromolecules per se is a very diverse process which results in different degradation rates in relation to the habitat and the abiotic parameters prevailing therein. As well as the abiotic boundary conditions, efficient biodegradation also requires correspondingly high compatibility between polymer and enzyme. Consequently, a high degradation rate can be achieved when the conditions prevailing in the habitat are optimal for the microorganisms involved and a specific interaction between polymer chain and enzyme is ensured. Crucial factors here are the temperature, the pH, the presence or absence of oxygen and the availability of nutrients, minerals and trace elements. According to the combination of these factors, the corresponding habitat is dominated by different consortia with a very variable number of microorganisms (total cell count: cells per unit volume; species diversity: number of microbial species in the habitat), and these lead to the different degradation rates described.

For the biodegradation of synthetic polymers, particular interest attaches to the "ecological systems", which find use in the context of biological waste treatment. As well as composting and the biological treatment of wastewater, particular mention should also be made of biogas-forming degradation under anaerobic conditions in biogas plants. In this context, as well as the metabolic end products of aerobic digestion ($H_2O$ and $CO_2$), methane is additionally formed, and this can be utilized later for generation of electrical power or be fed into the natural gas grid as biomethane. The process of anaerobic digestion (AD) is a complex multistage microbial reaction cascade (hydrolysis→acidogenesis→acetogenesis→methanogenesis), which combines the conversion of the polymers to monomers and the subsequent metabolic reactions of the intermediates extending as far as $H_2O$, $CO_2$ and $CH_4$. It is important here to mention that this process is conducted not by an individual, independent microorganism, but by a multitude of microorganisms each responsible for a corresponding component step of the reaction cascade. On the industrial scale, the process takes place either in plants for dry fermentation (dry matter>20-40% (w/w)) or for wet fermentation (dry matter<12-15% (w/w)). While wet plants are currently being used in Germany principally by farmers for biogas production from manure or renewable raw materials, plants for dry fermentation are also finding use in the elimination of organic waste in waste management. In the case of dry fermentation, a distinction can in turn be made between the continuously operated plug flow plants (continuous process; dry matter>20-30% (w/w)) and the discontinuously operated box fermenters (batch process; dry matter>30-40% (w/w)). This is just a selection of the available technologies. The efficiency of the respective process is based on how much biogas ($CO_2$ and $CH_4$ volume) can be obtained from the amount of substrate (carbon source) supplied and on the quality of the resulting biogas ($CH_4$ content). The methane formation potential of a substrate can thus be determined via the measurement of the methane formed within a defined unit of time and compared quantitatively with other substrates. For simplification and reproducibility of the method, a simple volume determination of the biogas formed is often conducted, in which the $CO_2$ is scrubbed out by means of sodium hydroxide solution beforehand. It is thus possible to determine the volume of methane formed by a direct route. Alternatively, it is also possible first to determine the total volume of the biogas, followed by the quantitative analysis of the biogas composition by means of a gas chromatograph. In view of later industrial use and better comparability, anaerobic digestion is generally considered over a period of not more than 2 months in all test methods.

Methods already described for determination of the biodegradability of polymers and other chemical substances can be found, for example, in the following ISO test methods:
ISO 11734
Water quality—Evaluation of the ultimate anaerobic biodegradability of organic compounds in digested sludge—Method by measurement of the biogas production ISO 15985
Plastics—Determination of the ultimate anaerobic digestibility and disintegration under high-solids anaerobic-digestion conditions—Method by analysis of released biogas
ISO 14853
Plastics—Determination of the ultimate anaerobic digestibility of plastic materials in an aqueous system—Method by analysis of released biogas
or in the VDI Guideline
VDI 4630
Fermentation of organic materials Characterization of the substrate, sampling, collection of material data, fermentation tests—the VDI guideline provides standardized rules and specifications for the conduct of fermentation experiments; this guideline makes it possible for the first time to achieve comparable, representative experimental results. The fermentation experiments detailed in the experimental section were therefore designed in analogy to VDI 4630.

Complete anaerobic fermentation of the inventive polymer mixtures was evidenced especially by the methods according to ISO 15985 and VDI 4630. The present process shall also comprise test methods which derive from the measurement principle, the underlying microorganisms and the concentrations of the microorganisms used in the two abovementioned test methods. Because of the ease of reproducibility and the usefulness of the results, the method according to VDI 4630 is very particularly preferred. The term "anaerobic digestibility" used in the present application is thus based primarily on VDI 4630.

The present invention accordingly relates more particularly to a process for complete anaerobic digestion of polymer mixtures of the composition:
a) 25 to 95% by weight, based on components a and b, of a polyhydroxyalkanoate selected from the group consisting of poly-4-hydroxybutyrate, poly-3-hydroxybutyrate, poly (3-hydroxybutyrate-co-3-hydroxyvalerate), poly(3-hydroxybutyrate-co-3-hydroxyhexanoate) and poly(3-hydroxybutyrate-co-4-hydroxybutyrate) and
b) 5 to 75% by weight, based on components a and b, of an aliphatic polyester comprising:
i) 65 to 100 mol %, based on components i to ii, of succinic acid or of a succinic acid derivative;
ii) 0 to 35 mol %, based on components i to ii, of an aliphatic $C_5$-$C_{33}$-dicarboxylic acid, of a corresponding acid derivative or of a mixture;
v) 98 to 100 mol %, based on components i to ii, of a $C_2$-$C_8$-alkylenediol or $C_2$-$C_6$-oxyalkylenediol;
vi) 0 to 2% by weight, based on the polymer obtainable from components i to iii, of at least one polyfunctional compound comprising at least two isocyanate, isocyanurate, oxazoline or epoxide groups or at least three alcohol or carboxylic acid groups;
wherein the anaerobic digestion can be determined by means of one of the processes according to VDI 4630 or ISO 15985. As mentioned above, the method according to VDI 4630 is particularly preferred.

The inoculation material used in VDI 4630 was an LUFA sludge. The content of dry matter was 3.7% of the fresh matter, and the ash made up 1.8% of the fresh matter (49.5% of the dry matter) and the organic matter (calcination loss) 1.9% of the fresh matter (50.5% of the dry matter); the pH was about 7.4 to 7.8.

In the method according to ISO 15985, the inoculum used originated from a fermentation plant for domestic waste and had the following composition: the content of dry matter was 20% of the fresh matter, and the ash made up 42.6% of the dry matter and the calcination loss 57.4%; the pH was about 8.7. The content of ammonium nitrogen was 1.55 g/kg; the content of volatile fatty acid was below the detection limit (<0.14 g/kg). This method was conducted with various mixtures of poly-3-hydroxybutyrate (PHB) and polybutylene succinate-co-sebacate (PBSSe with 5 mol % of sebacic acid, based on the dicarboxylic acids used), and likewise showed anaerobic digestion of the PBSSe.

The aforementioned complete anaerobic digestion of said polymer mixtures is understood to mean that not just mixture component a (polyhydroxyalkanoate) is degraded, which is already known from the literature, but also the aliphatic polyester b.

In the case of polymer mixtures having a proportion of greater than 20% by weight, preferably greater than 30% by weight and especially from 50 to 75% by weight of polymer component b), complete anaerobic digestion can be determined as follows:

Calculation of Biogas Potentials:
Basis:
Formula according to Buswell and Müller (1952):

$$C_aH_bO_c + \left(\frac{a}{1} - \frac{b}{4} - \frac{c}{2}\right)H_2O \rightarrow \left(\frac{a}{2} + \frac{b}{8} - \frac{c}{4}\right)CH_4 + \left(\frac{a}{2} - \frac{b}{8} + \frac{c}{4}\right)CO_2$$

This formula can be used to calculate how high the proportion of methane and carbon dioxide from a given substrate should be. The stoichiometric factors can additionally be used to calculate the amount of gas which should theoretically form (ideal gas law).

PBS ($C_8H_{12}O_4$; mass of this repeat unit: 172.178 g/mol):

$$C_8H_{12}O_4 + \left(\frac{8}{1} - \frac{12}{4} - \frac{4}{2}\right)H_2O \rightarrow \left(\frac{8}{2} + \frac{12}{8} - \frac{4}{4}\right)CH_4 + \left(\frac{8}{2} - \frac{12}{8} + \frac{4}{4}\right)CO_2$$

$$C_8H_{12}O_4 + 3H_2O \rightarrow 4.5CH_4 + 3.5CO_2$$

"1 mol" of PBS gives 8 mol of biogas ($CO_2$ and $CH_4$). Using the molar mass of the repeat unit, the following theoretical gas formation potential is obtained from 1 kg of PBS:

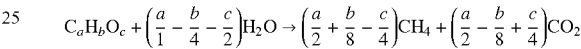

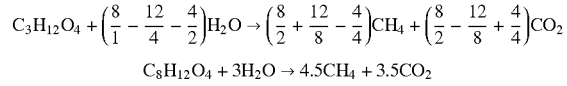

Under standard conditions, 1 mol of gas assumes a volume of 22.414 L. For 1 kg of PBS, this gives the following maximum/theoretical biogas potential:

$$V(\text{biogas})_{theoretical,max.} = 22.414 \frac{L}{mol} \times 46.464 \text{ mol} = 1041.4 \text{ L}$$

| Material | Mass of repeat unit | Empirical formula of repeat unit | $V(\text{biogas})_{theoretical,max.}$ |
|---|---|---|---|
| PHB | 86.089 g/mol | $C_4H_6O_2$ | 1041 L/kg |
| PBS | 172.178 g/mol | $C_8H_{12}O_4$ | 1041 L/kg |

| Material | Mass of repeat unit | Empirical formula of repeat unit | V(biogas)$_{theoretical,max.}$ |
|---|---|---|---|
| PBSA 20% adipic acid | 177.789 g/mol | $C_{8.4}H_{12.8}O_4$ | 1059 L/kg |
| PBSSe 5% sebacic acid | 176.386 g/mol | $C_{8.3}H_{12.6}O_4$ | 1054.7 L/kg |

PBSA:

$$C_{8.4}H_{12.3}O_4 + \left(\frac{8.4}{1} - \frac{12.8}{4} - \frac{4}{2}\right)H_2O \rightarrow$$
$$\left(\frac{8.4}{2} + \frac{12.8}{8} - \frac{4}{4}\right)CH_4 + \left(\frac{8.4}{2} - \frac{12.8}{8} + \frac{4}{4}\right)CO_2$$
$$C_{8.4}H_{12.8}O_4 + 3.2H_2O \rightarrow 4.8CH_4 + 3.6CO_2$$

"1 mol" of PBSA gives 8.4 mol of biogas.

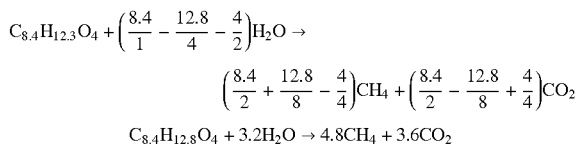

$$1000 \text{ g } PBSA \div 177.789 \frac{\text{g}}{\text{mol}} = 5.625 \text{ mol } PBSA$$
$$5.625 \text{ mol } PBSA \rightarrow 47.247 \text{ mol biogas}$$
$$V(\text{biogas})_{theoretical,max,} = 22.414 \frac{L}{\text{mol}} \times 47.247 \text{ mol} = 1059 \text{ L}$$

PBSSe:

$$C_{8.3}H_{12.5}O_4 + \left(\frac{8.3}{1} - \frac{12.6}{4} - \frac{4}{2}\right)H_2O \rightarrow$$
$$\left(\frac{8.3}{2} + \frac{12.6}{8} - \frac{4}{4}\right)CH_4 + \left(\frac{8.3}{2} - \frac{12.6}{8} + \frac{4}{4}\right)CO_2$$
$$C_{8.3}H_{12.6}O_4 + 3.15H_2O \rightarrow 4.725CH_4 + 3.575CO_2$$

"1 mol" of PBSSe gives 8.3 mol of biogas.

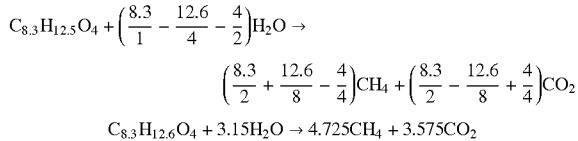

$$1000 \text{ g } PBSA \div 176.386 \frac{\text{g}}{\text{mol}} = 5.669 \text{ mol } PBSSe$$
$$5.669 \text{ mol } PBSSe \rightarrow 47.056 \text{ mol biogas}$$
$$V(\text{biogas})_{theoretical,max,} = 22.414 \frac{L}{\text{mol}} \times 47.056 \text{ mol} = 1054.7 \text{ L}$$

Complete anaerobic digestion is understood to mean a digestion rate (biogas evolution measured to VDI 4630 in 28 days) of the polymer mixture a+b, based on the polymer component a, of greater than 90%. Examples of this are given in table 1.

The complete anaerobic digestion of polymer mixtures having a high content of polymer component a of greater than 80% and especially greater than 90% is determined as follows. It is assumed that the proportion of polymer component a has been 100% degraded. The amount of biogas determined experimentally for this purpose is subtracted from the amount of biogas formed, and the excess is ascribed to the digestion of polymer component b. This value can be used to check, on the basis of values tabulated above, whether component b has been degraded to an extent of greater than 90%.

In the case of polymer mixtures comprising 80% by weight or more of polymer component b, based on components a and b, are not completely degraded according to the abovementioned criteria. As already mentioned, polymer component b as a pure substance is not anaerobically degraded at all.

The biodegradable polyesters and polyester mixtures mentioned at the outset are suitable for production of films and film strips for meshes and fabrics, tubular films, chill roll films with or without alignment in a further process step, with or without metallization or SiOx coating.

Polymer mixtures a and b and optionally additionally thermoplasticized starch or fillers can be used to produce thin films having a layer thickness of 5 to 45, preferably 8 to 40 and especially 10 to 35 μm.

More particularly, the films comprising polymer components a) and b) are suitable for tubular films and stretch films. Possible applications here are basal fold bags, lateral seam bags, carrier bags with a hole grip, shrink labels or vest-type carrier bags, inliners, heavy-duty sacks, freezer bags, biowaste bags, agricultural films (mulch films), film bags for packaging of foods, peelable closure film-transparent or opaque-weldable closure film-transparent or opaque, sausage skin, salad film, freshness retention film (stretch film) for fruit and vegetables, meat and fish, stretch film for wrapping of pallets, film for nets, packaging films for snacks, chocolate bars and muesli bars, peelable lid films for dairy packaging (yoghurt, cream, etc.), fruit and vegetables, semirigid packaging, for example for smoked sausage and cheese.

Due to their barrier properties with respect to oxygen and aromas, which are excellent for biodegradable films, the films mentioned are uniquely suitable for packaging of meat, poultry, meat products, processed meat, sausages, smoked sausage, seafood, fish, crab meat, cheese, cheese products, desserts, pies, for example with meat, fish, poultry, tomato filling, pastes and bread spreads; bread, cakes, other bakery products; fruit, fruit juices, vegetables, tomato puree, salads; animal food; pharmaceutical products; coffee, coffee-like products; milk powder or cocoa powder, coffee whitener, baby food; dried foods; jams and jellies; bread spreads, chocolate cream; ready meals. For further information see reference in "Food Processing Handbook", James G. Brennan, Wiley-VCH, 2005.

The films additionally have very good adhesion properties. As a result, they are of excellent suitability for coating of paper, for example for paper cups and paper plates. For the production thereof, both extrusion coating and lamination processes are suitable. A combination of these processes, or coating by spraying, with a coating bar or by immersion, is also conceivable.

In many countries, biomass, comprising biowaste, green waste, out of date and inedible food and drink, peelings, stalks etc. from what is called domestic waste, and also refuse, residues from the growing of foods and in the production of foods, are disposed of at refuse tips. In the course of rotting at the tips, not inconsiderable amounts of methane, a harmful greenhouse gas, pass unhindered into the atmosphere. Incineration of the biomass is also not a good alternative due to the high water content thereof and the associated poor energy balance in the course of incineration. The disposal of the biomass in composting plants and especially biogas plants (additional recovery of biogas, which can be used as an energy source) constitutes the best solution in terms of overall environmental balance. To date, the biomass has often been collected by means of paper bags or newspaper, which soak through easily, or hygienic and breathable packaging was used, for example refuse bags or packaging for foods, but these cannot be degraded in biogas plants under the anaerobic conditions which exist therein.

With the present polymer mixtures, it is for the first time possible to provide packaging (for foods, and also waste bags for biowaste) which enables disposal together with the biomass collected therein in a biogas plant. In municipalities having facilities for disposal in a biogas plant, the following process constitutes an alternative of very great interest:

A process for disposing of biomass in a biogas plant, in which in a first step the biomass is collected or dispensed in a package comprising polymer mixtures of the composition:
a) 25 to 95% by weight of a polyhydroxyalkanoate selected from the group consisting of poly-4-hydroxybutyrate, poly-3-hydroxybutyrate, poly(3-hydroxybutyrate-co-3-hydroxyvalerate), poly(3-hydroxybutyrate-co-3-hydroxyhexanoate) and poly(3-hydroxybutyrate-co-4-hydroxybutyrate) and
b) 5 to 75% by weight of an aliphatic polyester comprising:
  i) 65 to 100 mol %, based on components i to ii, of succinic acid or of a succinic acid derivative;
  ii) 0 to 35 mol %, based on components i to ii, of an aliphatic $C_8$-$C_{36}$-dicarboxylic acid, of a corresponding acid derivative or of a mixture;
  iii) 98 to 100 mol %, based on components i to ii, of a $C_2$-$C_8$-alkylenediol or $C_2$-$C_8$-oxyalkylenediol;
  iv) 0 to 2% by weight, based on the polymer obtainable from components i to iii, of at least one polyfunctional compound comprising at least two isocyanate, isocyanurate, oxazoline or epoxide groups or at least three alcohol or carboxylic acid groups;
in a second step the biomass in this package is collected by a waste management company, and in a third step the biomass in this package is sent to anaerobic fermentation in a biogas plant.

Performance Testing:

The molecular weights Mn and Mw of the semiaromatic polyesters were determined to DIN 55672-1. Eluent: hexafluoroisopropanol (HFIP)+0.05% by weight trifluoroacetic acid Ka salt; the calibration was effected with narrow-distribution polymethyl methacrylate standards. The viscosity numbers were determined to DIN 53728 Part 3, Jan. 3, 1985, capillary viscometry. An Ubbelohde M-II microviscometer was used. The solvent used was the mixture: phenol/o-dichlorobenzene in a weight ratio of 50/50.

Modulus of elasticity and elongation at break were determined by means of a tensile test to ISO 527-3:2003.

Tear propagation resistance was determined by an Elmendorf test to EN ISO 6383-2:2004 on specimens with constant radius (tear length 43 mm).

In a puncture resistance test, the maximum force and the puncture energy of the polyesters were measured:

The test machine used is a Zwick 1120 equipped with a spherical punch with a diameter of 2.5 mm. The sample, a circular piece of the film to be tested, was clamped perpendicularly with respect to the test punch, and the punch was moved at a constant test velocity of 50 mm/min through the plane clamped by the clamping device. Force and elongation were recorded during the test and were used to determine penetration energy.

The anaerobic biodegradability of the polyester mixtures and of the reference polymers was determined as follows:

The test setup and the procedure were appropriate to the corresponding method "4.1.1 Bestimmung der Biogas- and Methanausbeute in Gärtests" [Determination of the biogas and methane yields in fermentation tests] from the VDLUFA Methodenbuch VII (Umweltanalytik). The reaction vessels (fermenters) used for the determination of the biogas formation potential (anaerobic digestion) were glass vessels with a capacity of 5 l, which could be sealed gas-tight with a butyl septum and a screwtop lid. The process temperature was kept constant by means of a water bath and thermostat, in accordance with the experimental conditions (mesophilic: 38±1° C.; thermophilic: 55±1° C.). The test mixtures were mixed discontinuously, once per day. The fermenter contents used were seed material which originated from measurements of biogas yields in a batch process and had been prepared under defined conditions (to VDI 4630). The inoculation material used was an LUFA sludge. The content of dry matter was 3.7% of the fresh matter, and the ash made up 1.8% of the fresh matter (49.5% of the dry matter) and the organic substance (calcination loss) 1.9% of the fresh matter (50.5% of the dry matter); the pH was about 7.4 to 7.8. The microorganisms present, prior to commencement of the experiment, were conditioned under anaerobic conditions without supply of substrate for a period of 5 weeks. In preparation, the fermenters were charged with 4.5 l of conditioned seed material, 30 g of the appropriate test substance were added (corresponds to a ratio of seed material oDM to test substance oDM of 3.375:1 (w/w)), the fermenter was sealed gas-tight and the gas phase of the fermenter was replaced with nitrogen. On commencement of the experiment, the biogas formed was collected in a gas collection bag, which was connected via gas-tight hose connections to the gas space of the fermenter. The volume of biogas formed was measured discontinuously; the gas composition was determined by IR measurement ($CH_4$, $CO_2$, $O_2$) and by means of electrochemical sensors ($H_2S$) in a gas chromatograph.

Feedstocks:

Polymer Component a (Polyhydroxyalkanoate)

Polyester A1

Poly-3-hydroxybutyrate from PHB-Isa (trade name Biocycle 1000).

Polymer Component b (Aliphatic Polyester)

Polyester B1

Bionolle® 1001, polybutylene succinate from Showa Highpolymer

Polyester B2

Bionolle® 3001 polybutylene succinate-co-adipate from Showa Highpolymer

Polyester B3

Polybutylene succinate sebacate, which was prepared as follows: 165.2 kg of succinic acid (95 mol %), 14.9 kg of sebacic acid (5 mol %), 172.5 kg of 1,4-butanediol and 0.26 kg of glycerol were mixed together with 0.031 kg of tetrabutyl orthotitanate (TBOT), with a molar ratio between alcohol components and acid component of 1.30. The reaction mixture was heated to a temperature of 200° C. and reacted at this temperature for 2.75 h, before vacuum was applied and another 0.062 kg of tetrabutyl orthotitanate (TBOT) was added. With commencement of vacuum, the temperature was increased to 250-260° C. and the excess dihydroxyl compound was distilled off over a period of 11 h (final vacuum approx. 3 mbar). On attainment of the desired final viscosity, the polycondensation was stopped by breaking the vacuum and cooling to approx. 180-210° C., and the prepolyester was chain-extended at 240-250° C. with 1 part by weight of hexamethylene diisocyanate based on the polymer mixture and pelletized. The polyester B3 thus obtained had a melting temperature of 107° C. and a molecular weight (Mn) of 27 700 g/mol, molecular weight (Mw) of 120 000 g/mol).

Examples E1 to E7 and Comparative Examples C1 to C4

The proportions of PHB A1 and polyesters B1, B2 and B3 specified in table 1 were compounded in an FTS 16 [in experiments C4, E6 and E7 in an MC26] co-rotatory twin-screw extruder (constructed in-house) (l/d=25) at a melt temperature (head zone) of approx. 170° C., a speed of 200 min$^{-1}$ and a throughput of 1.5 kg/h, discharged as extrudate pellets.

All samples listed in table 1 (C1-C4 and E1-E7), for the anaerobic digestion tests, were comminuted to powder using a turbo mill (from Pallmann; PPL 18).

For random powder samples, the particle size distribution was determined with a Malvern Mastersizer 2000. For example, for mixture E4 (70% PBSA and 30% PHB), the measured characteristics ($d_{10/60/90}$) were 154 μm/360 μm/746 μm. For all samples analyzed, the $d_{90}$ value was below 1000 μm. This means that 90% by volume of the powder has a particle size less than 1000 μm.

B3 in examples E1-E7 led, however, to polymer mixtures which exhibited much higher biogas yields in the degradation test than would have been theoretically expected. For example, the biogas yield in example E1 exceeded the theoretically assumed maximum value by approx. 90% after only 14 days. In the case of addition of A1 to B2 too, after 14 days, unexpected rises in the biogas yield by about 95% (example E2; 50% A1), 143% (example E3; 40% A1) and 175% (example E4; 30% A1) were measured compared to the expected maximum yields. This is surprising given the comparatively small polyhydroxyalkanoate content A1. If the polyhydroxyalkanoate content A1 is reduced further (example E5; 20% A1), degradation is still observed above the expected level over the course of the experiment. However, the degradation rate is much reduced.

A rise in the biogas yields was also observable after addition of A1 to B3. Here, the real biogas yield exceeded the theoretical biogas yield after 14 days by 84% (example E6; 50% A1) and 180% (example E7; 30% A1).

These results lead to the conclusion that the addition of component A1 having excellent anaerobic digestibility in the

TABLE 1

| | Example | | | | | | | | | | |
|---|---|---|---|---|---|---|---|---|---|---|---|
| | C1 | C2 | C3 | C4 | E1 | E2 | E3 | E4 | E5 | E6 | E7 |
| Comp. A1 [% by wt.] | 100 | | | | 50 | 50 | 40 | 30 | 20 | 50 | 30 |
| Comp. B1 [% by wt.] | | 100 | | | 50 | | | | | | |
| Comp. B2 [% by wt.] | | | 100 | | | 50 | 60 | 70 | 80 | | |
| Comp. B3 [% by wt.] | | | | 100 | | | | | | 50 | 70 |
| Biogas evol.* [l/kg] | 1005 | 7 | 15 | 0 | 963 | 983 | 977 | 833 | 111 | 926 | 848 |
| Biogas evol.** [l/kg] | 1005 | 7 | 18 | 0 | 974 | 996 | 991 | 943 | 277 | 938 | 896 |
| Biogas evol.*** [l/kg] | 1005 | 8 | 20 | 0 | 992 | 1003 | 997 | 972 | 388 | 941 | 906 |
| Methane content in biogas at end of experiment [%] | 56.2 | — | — | — | 56.6 | 56.6 | 56.9 | 54.4 | 58.2 | 57.8 | 45.8 |

*Biogas evolution after 14 days
**Biogas evolution after 28 days
***Biogas evolution after 42 days The data depicted in table 1 show the biogas yields ($CO_2+CH_4$) of the various polymer mixtures after an incubation period of 14, 28 and 42 days under mesophilic conditions at 38° C. In the control experiments C1, C2, C3 and C4, the different individual components of the polymer mixtures were used in the degradation test. For component A1 (PHB, see C1), with a biogas evolution of 1005 l/kg after only 14 days, full anaerobic biodegradation is observed. In contrast, after 42 days, no significant degradation in components B1 (PBS, see C2), B2 (PBSA, see C3) and B3 (PBSSe, see C4) was observed in the control experiments.

It was consequently assumed that, in the polymer mixtures examined (E1-E7), only component A1 can be biodegraded. Thus, maximum biogas yields of 503 l/kg (E1; 50% A1), 503 l/kg (E2; 50% A1), 402 l/kg (E3; 40% A1), 302 l/kg (E4; 30% A1), 201 l/kg (E5; 20% A1), 503 l/kg (E6; 50% A1) and 302 l/kg (E7; 30% A1) were to be expected. Surprisingly, the addition of component A1 to B1, B2 and ratios claimed induces a rise of industrial relevance in the biodegradability or—as defined above—complete anaerobic digestion of components B1, B2 and B3.

The invention claimed is:

1. A process for disposing of biomass in a biogas plant, the process comprising:
   A) collecting or dispensing the biomass into a package, the package prepared from a composition comprising a polymer mixture;
   B) transporting the package in a waste management vehicle to a biogas plant; and
   C) fermenting the package anaerobically in a biogas plant to make biogas,
   wherein the polymer mixture in step A) comprises: (1) a polyhydroxylalkanoate of 25 to 95% by weight; and (2) an aliphatic polyester of 5 to 75% by weight,
   wherein the polyhydroxylalkanoate of (1) is selected from the group consisting of poly-4-hydroxybutyrate, poly- 3-hydroxybutyrate, poly(3-hydroxybutyrate-co-3-hydroxyvalerate), poly(3-hydroxybutyrate-co-3-hydroxyhexanoate), and poly(3-hydroxybutyrate-co-4-hydroxybutyrate, wherein the aliphatic polyester of (2) comprises: (i) a diol/diacid component; and (ii) at least one polyfunctional compound of 0 to 2% by weight, wherein the diacid component in the diol/diacid component of (i) is of 65 to 100 mol % of succinic acid, or a derivative thereof, and 0 to 35 mol % of an aliphatic $C_5$-$C_{36}$-dicarboxylic acid, or a derivative thereof, or a mixture of the dicarboxylic acid and the derivative, wherein the diol component in the diol/diacid component of (i) is a $C_2$-$C_8$-alkylenediol or $C_2$-$C_6$-oxyalkylenediol, wherein the diol/diacid component of (i) has a diol/diacid molar ratio between 0.98:1 and 1:1, and wherein the at least one polyfunctional compound of (ii) comprises at least two isocyanate, isocyanurate, oxazoline or epoxide groups, or at least three alcohol or carboxylic acid groups.

2. The process according to claim 1, wherein the polymer mixture composition comprises:
   a) 25 to 50% by weight of the polyhydroxyalkanoate and
   b) 50 to 75% by weight of the aliphatic polyester.

3. The process according to claim 1, wherein the aliphatic polyester b) comprises:
   (i) 75 to 98 mol % of succinic acid or of a succinic acid derivative;
   (ii) 2 to 25 tool % of the aliphatic Cs-C36-dicarboxylic acid selected from an adipic acid, suberic acid, azelaic acid, sebacic acid and/or brassylic acid: or of a corresponding acid derivative of each acid thereof; and
   (iii) 0.05 to 2% by weight of the at least one polyfunctional compound.

4. The process according to claim 1, wherein the polyhydroxyalkanoate is selected from poly(3-hydroxybutyrate-co-3-hydroxyvalerate), poly(3-hydroxybutyrate-co-3-hydroxyhexanoate) or poly(3-hydroxybutyrate-co-4-hydroxybutyrate).

5. The process according to claim 4, wherein the polyhydroxyalkanoate is poly(3-hydroxybutyrate-co-3-hydroxyvalerate.

6. The process according to claim 4, wherein the polyhydroxyalkanoate is poly(3-hydroxybutyrate-co-3-hydroxyhexanoate).

7. The process according to claim 4, wherein the polyhydroxyalkanoate is poly(3-hydroxybutyrate-co-4-hydroxybutyrate).

8. The process according to claim 1, wherein the package composition further comprises 5 to 50% by weight of thermoplasticized starch.

9. The process according to claim 1, wherein the polyhydroxyalkanoate is poly-3-hydroxybutyrate.

10. The process according to claim 1, wherein the aliphatic polyester b) comprises:
    75 to 98 mol % of succinic acid or of a succinic acid derivative;
    2 to 25 mol % of the aliphatic $C_5$-$C_{36}$-dicarboxylic acid selected from an adipic acid, suberic acid, azelaic acid, sebacic acid and/or brassylic acid, or of a corresponding acid derivative of each acid thereof.

11. The process according to claim 1, wherein the composition in the package is in the form of a thin film having a layer thickness of 8 to 40 μm.

12. The process according to claim 1, wherein the package is in a product form selected from basal fold bag, lateral seam bag, carrier bag with a hole grip, shrink label, vest-type carrier bags, inliners, heavy-duty sacks, freezer bags, biowaste bags, agricultural films, mulch films, or film bags for packaging of foods.

* * * * *